United States Patent [19]

Chan et al.

[11] Patent Number: 5,028,624

[45] Date of Patent: Jul. 2, 1991

[54] INTRAOCULAR PRESSURE REDUCING 9,15-DIACYL PROSTAGLANDINS

[75] Inventors: Ming F. Chan, Santa Ana; David F. Woodward, El Toro, both of Calif.

[73] Assignee: Allergan, Inc., Irvine, Calif.

[21] Appl. No.: 584,370

[22] Filed: Sep. 18, 1990

Related U.S. Application Data

[63] Continuation of Ser. No. 386,312, Jul. 27, 1989, abandoned.

[51] Int. Cl.$^5$ .......................................... A61K 31/215
[52] U.S. Cl. .................................... 514/530; 514/913
[58] Field of Search ................................ 514/530, 913

[56] References Cited

U.S. PATENT DOCUMENTS

| | | |
|---|---|---|
| 4,001,306 | 1/1977 | Morozowich et al. . |
| 4,060,540 | 11/1977 | Bernady et al. ...................... 556/441 |
| 4,599,353 | 7/1986 | Bito ..................................... 514/530 |
| 4,822,819 | 4/1989 | DeSantis et al. . |
| 4,824,857 | 4/1989 | Goh et al. . |
| 4,883,819 | 11/1989 | Bito, II . |

FOREIGN PATENT DOCUMENTS

| | | |
|---|---|---|
| 0286903 | 3/1987 | European Pat. Off. . |
| 2627671 | 1/1977 | Fed. Rep. of Germany . |
| 8806448 | 7/1988 | PCT Int'l Appl. . |
| 8903384 | 4/1989 | Sweden . |

OTHER PUBLICATIONS

Starr, *Exp. Eye Res.* 11, 170–177 (1971).
Zajacz et al., *The Eye: Reproduction, Obstetrics and Gynecology* 4, 316 (1976).
Keun Kim *Investigative Ophthalmology* 14, 36 (1975).
Camras et al., *Invest. Ophthalmol. Visual Sci.* 16, 1125 (1977).
Woodward et al., *Invest. Ophthalmol. Visual Sci.* 30, 1838 (1989).
Nilsson et al., *Exp. Eye Res.* 48, 707 (1989).
Bito, *Arch. Ophthalmol.* 105, 1036 (1987).
Siebold et al., *Prodrug.* 5, 3 (1989).

*Primary Examiner*—Stanley J. Friedman
*Assistant Examiner*—Zohreh A. Fay
*Attorney, Agent, or Firm*—Martin A. Voet; Robert J. Baran

[57] ABSTRACT

Disclosed is an intraocular pressure reducing method and composition wherein 9,15-diacyl prostaglandins are contained in a pharmaceutically acceptable excipient for topical application on the surface of the eye.

26 Claims, No Drawings

INTRAOCULAR PRESSURE REDUCING 9,15-DIACYL PROSTAGLANDINS

This application is a continuation of application Ser. No. 07/386,312, filed 07/27/89, now abandoned.

BACKGROUND OF THE INVENTION

The present invention relates to a means for reducing or maintaining intraocular pressure. More particularly it relates to a method and composition for reducing or maintaining intraocular pressure involving the administration of a composition containing a 9,15-diacyl ester prostaglandin in an ophthalmically acceptable carrier.

The method and compositions of the present invention are particularly useful for the management of glaucoma, a disease of the eye characterized by increased intraocular pressure. On the basis of its etiology, glaucoma has been classified as primary or secondary. For example, primary glaucoma in adults, congenital glaucoma, may be either chronic open-angle or acute or chronic angle-closure. Secondary glaucoma results from pre-existing ocular diseases such as uveitis, intraocular tumor or an enlarged cataract.

The underlying causes of primary glaucoma are not yet well known. The increased intraocular tension is due to obstruction of aqueous humor outflow. In chronic open-angle glaucoma, the anterior chamber and its anatomic structures appear normal, but drainage of the aqueous humor is impeded. In acute and chronic angle-closure glaucoma, the anterior chamber is shallow, the filtration angle is narrowed and the iris may obstruct the trabecular meshwork at the entrance to the canal of Schlemm. Dilation of the pupil may push the root of the iris forward against the angle or may produce pupillary block and thus precipitate an acute attack. Eyes with narrow anterior chamber angles are predisposed to acute angle-closure glaucoma attacks of varying degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptomatic for years before progressing to rapid loss of vision. In cases where surgery is not indicated, topical $\beta$-adrenoceptor antagonists have traditionally been the drugs of choice for treating glaucoma.

Certain eicosanoids, specifically C-1 esters of certain prostaglandins, have been reported to possess ocular hypotensive activity. However, prostaglandin ocular hypotensives generally suffer from the disadvantage of inducing conjunctival hyperemia of varying severity and duration, smarting, and foreign body sensation, as well as presenting solubility problems in certain ophthalmically advantageous carriers.

This invention relates to derivatives of the known prostaglandins formulated in a pharmaceutically acceptable vehicle, and ophthalmic use of those prostaglandins. The present invention is advantageous in that ocular hypotension is achieved with a reduced incidence of ocular surface hyperemia.

SUMMARY OF THE INVENTION

In accordance with one aspect of the present invention, there is provided a method of treating ocular hypertension which comprises applying to the eye an amount sufficient to treat ocular hypertension of a 9,15 diacyl compound represented by formula I.

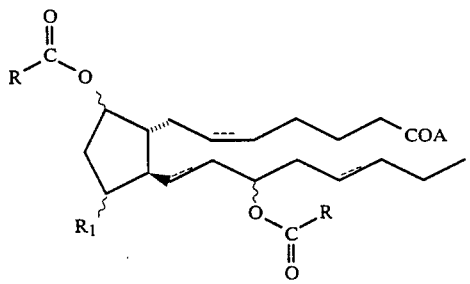

In formula I, the dashed bond represents a double bond which can be in the cis or trans configuration, or a single bond; A is —OH, —O$^-$X$^+$ where X$^+$ is a pharmaceutically acceptable cation, or —OR$_2$ where R$_2$ is lower alkyl; R$_1$ is —OH or =O; and the R groups are independently an acyclic hydrocarbon, saturated or unsaturated, having from 1 to 20 carbon atoms, or —(CH$_2$)$_n$R$_3$ where n is 0–10 and R$_3$ is a hydrocarbon ring of from 3 to 7 carbon atoms or an aromatic or heteroaromatic ring.

In accordance with another aspect of the present invention, there is provided an ophthalmically acceptable composition for reducing ocular hypertension which comprises at least one 9,15-diacyl prostaglandin described above present in an ophthalmically acceptable excipient for topical application to the eye. Such as excipient is one which does not have a deleterious or untoward effect on the eye when used in normal treatment regimens.

Further features and advantages of the present invention will become apparent from the detailed description of preferred embodiments which follows, taken together with the examples and claims appended hereto.

DETAILED DESCRIPTION OF THE INVENTION

It has been discovered that certain prostaglandins lower intraocular pressure in man and other mammals when applied topically to the eye. Although the precise mechanism is not yet knwon, prostaglandins appear to increase aqueous humor outflow to restore a normotensive or hypotensive state. However, topical application of prostaglandins generally causes side effects such as conjunctival hyperemia, smarting and foreign body sensation which range in degree from undesirable to unacceptable, depending upon the particular patient and dosage necessary to produce a sufficient pressure regulating effect.

In the foregoing illustration, as well as those provided hereinafter, wavy line attachments indicate either the alpha ($\alpha$) or beta ($\beta$) configuration. The dotted lines on bonds between carbons 5 and 6 (C-5), between carbons 13 and 14 (C-13), and between carbons 17 and 18 (C-17) indicate a single or double bond which can be in the cis or trans configuration. If two solid lines are used at C-5, C-13, or C-17, it indicates a specific configuration for that double bond. Hatched lines used at position C-9, C-11 and C-15 indicate the α configuration. If one were to draw the β configuration, a solid triangular line would be used at any of these three positions.

The naturally occurring stereochemistry of PGF$_{2\alpha}$ includes the C-9, C-11 and C-15 position hydroxyl groups in the α configuration. In the compositions of the present invention, however, esters of prostaglandins having the C-9 or C-11 or C-15 hydroxyl group in the β configuration are also contemplated.

The 9,15-diacyl prostaglandins suitable for use in this invention can comprise any of a variety of acyl substituents at the two 9 and 15 positions. As per formulas I, either R group can be an aliphatic acyclic hydrocarbon having from one to twenty carbon atoms, inclusive. Preferably each R group has from one to ten carbon atoms. Most preferably each R group is the same and is methyl, ethyl, propyl, butyl, pentyl, or an isomeric form thereof. The prefered isomeric forms are the isopropyl, butyl, isobutyl and t-butyl isomers.

Alternatively each R group can comprise a cyclic component. In particular, either R group can be $(CH_2)_nR_3$ where n is 0-10 and $R_3$ is a saturated or unsaturated ring, perferably a saturated ring having from three to seven carbon atoms, inclusive, or an aromatic or heteroaromatic ring of 5 to 7 carbon atoms, and having oxygen, nitrogen or sulfur in the case of a heteroaromatic ring. Preferably n is 0-4.

In all formulations provided herein broken line attachments to the cyclopentane ring indicate substituents in the α configuration. Thickened solid line attachments to the cyclopentane ring indicate substituents in the β configuration. For instance, PGF$_\beta$ compounds have the same structure as the above PGF$_\alpha$ compounds, except that the hydroxyl at the C-9 position is in the β configuration. Also, the broken line attachment of the hydroxyl group to the C-15 carbon atom signifies the α configuration; therefore, compounds with the epi configuration for the hydroxyl group at C-15 are designated by using 15β and if there is no indication of the β configuration, the configuration is assumed to be α.

The preferred compounds of this invention are those which have the following structures.

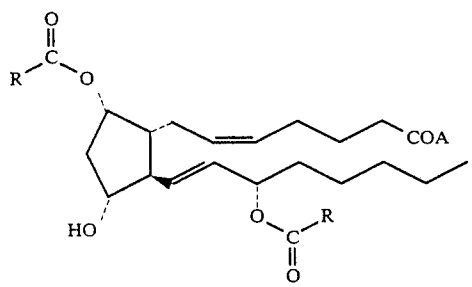

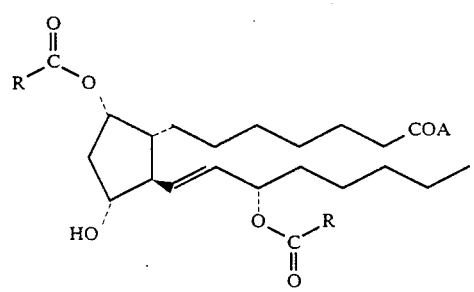

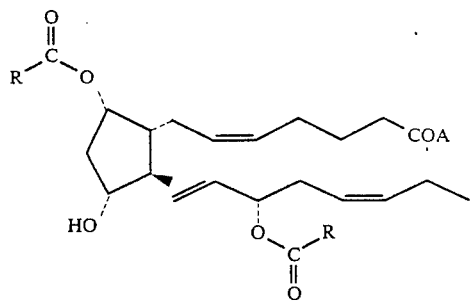

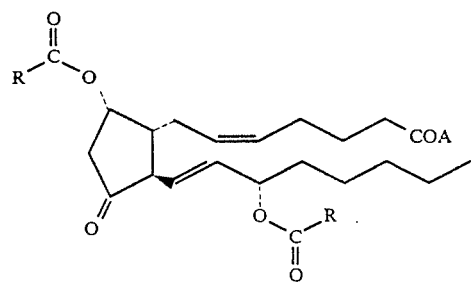

Within this preferred group, the most preferred compounds are those where both R groups are the same and are —CH$_3$, —CH$_2$CH(CH$_3$)$_2$—CH(CH$_3$)$_2$, or —C(CH$_3$)$_3$.

Where A is in the salt form of O$^-$X$^+$, X$^+$ may be any pharmaceutically acceptable cation, thus forming a pharmacuetically acceptable salt. Such a salt may be prepared for any compound in this disclosure having a functionality capable of forming such a salt, in particular, the carboxylic acid group at C$_1$ of the prostaglandins disclosed herein. A pharmaceutically acceptable salt is any salt which retains the activity of the parent compound and does not impart any deleterious or undesirable effect on the subject to which it is administered and in the context in which it is administered.

These salts may be derived from an organic or inorganic base. Such a salt may be a mono- or polyvalent ion. Of particular interest are the inorganic ions, sodium, potassium, calcium, magnesium and zinc. Organic ammonium salts may be made with amines, such as mono-, di-, and trialkyl amines or ethanolamines. Salts may also be formed with caffeine, tromethamine and similar molecules.

In another aspect, this invention relates to a composition which can be applied topically to the eye to lower intraocular pressure. This composition comprises one or more of the foregoing 9,15-diacyl prostaglandins therein. The composition may comprise any of a variety of ophthalmically acceptable carriers as will be known to those skilled in the art of ocular drug delivery. A preferred method of application would be topical, in a pharmaceutically acceptable topical formulation. Such a carrier may be comprised of a saline and/or co-solvent, containing pharmaceutically required or advantageous adjuvants, along with an effective dose of the intraocular pressure reducing drug.

In accordance with a preferred embodiment of the present invention, the carrier comprises a solution having polysorbate 80-10 mM TRIS in the range of from about 0.05-1.0% by weight, and preferably about 0.1%, which is particularly suited for administration in the form of a liquid eye drop. This carrier may additionally comprise pharmaceutically advantageous adjuvants such as a preservative, antibiotic/antimycotic agents, pH buffers or osmotic balancers. In a preferred embodiment of the present invention, the intraocular pressure-reducing agent comprises a derivative of $PGF_{2\alpha}$, preferably one or a combination of the 9,15-diacetyl, 9,15-diisobutyryl, 9,15-divaleryl, 9,15-diisovaleryl or 9,15-dipivaloyl derivatives of $PGF_{2\alpha}$.

The optimal concentration of the prostaglandin derivative is a function of a variety of factors, such as desired frequency of application and duration of effect, level of adverse side effects and considerations implicated by the chemical nature of the carrier. In general, however, concentrations are contemplated within the range of from about 0.0001% to 1%, preferably from 0.001% to 0.1% by weight in relation to the pharmaceutically acceptable carrier.

The invention can be more fully understood by the following examples. All temperatures are in degrees centigrade.

EXAMPLE 1

Preparation the 9,15-Dipivaloyl $PGF_{2\alpha}$

Prostaglandin $F_{2\alpha}$ (from Chinoin Chemical Co., 40.4 mg, 0.114 mmol) was suspended in methylene chloride (2 ml) and cooled in an ice bath. A solution of diazomethane in ether was added dropwise to the above suspension until a yellow color persists. The solution was stirred at 25° C. for 30 min and the solvents were evaporated to give the $PGF_{2\alpha}$ methyl ester.

$^1$HNMR(300 MHz, CDCl$_3$): δ5.3–5.6 (4H, m), 4.16 (1H, br s), 4.06 (1H, q, J=6.51 Hz), 3.93 (1H, br s), 3.67 (3H, s), 2.70 (1H, br s), 2.32 (2H, t, J=7.3 Hz), 1.2–2.4 (21H, m) and 0.88 ppm (3H, distorted t, J=6 Hz).

The crude methyl ester from above was heated under reflux with butylboronic acid (14 mg, 0.137 mmol) in methylene chloride (0.25 ml) for 30 min. The solvent was removed under reduced pressure and replaced with dry benzene. The benzene was again evaporated under reduced pressure. This process was repeated twice to remove traces of water by azeotropic distillation. The crude boronate was dissolved in 0.2 ml dry pyridine and treated with trimethylacetyl chloride (42 μl, 0.34 mmol) at 25° C. 4-Dimethylaminopyridine was added and the mixture was stirred at 25° C. for 14 hours. The volatiles were evaporated in vacuo. The residue was dissolved in ethyl acetate (10 ml) and washed with 10% citric acid (7 ml). The aqueous phase was back-extracted with ethyl acetate (3×7 ml) and the combined organic extract was washed once with brine (7 ml) and dried over magnesium sulfate. After removal of solvent under reduced pressure the residue was stirred in 3 ml methanol at 25° C. After 2 hours, the solvent was removed, replaced with a fresh batch of methanol and stirred for an additional 2 hours. The solvents were evaporated off and the crude product (50.7 mg) was chromatographed on silical gel using 50–60% ethyl acetate/hexane as eluent to give 15-pivaloyl $PGF_{2\alpha}$ methyl ester.

$^1$H NMR (300 MHz, CDCl$_3$): δ5.3–5.6 (4H, m), 5.18 (1H, q, J=6.5 Hz), 4.19 (1H, br s), 3.95 (1H, br s), 3.67 (3H, s), 2.33 (2H, t, J=7 Hz), 1.2–2.4 (20H, m) 1.19 (9H, s) and 0.88 ppm (3H, distorted t, J=7 Hz).

15-Pivaloyl $PGF_{2\alpha}$ methyl ester (33.9 mg, 0.075 mmol) prepared as described above was dissolved in methylene chloride (0.2 ml) and treated with triethylamine (20 μl, 0.142 mmol) and 4-dimethylaminopyridine (1.5 mg, 0.01 mmol) at 25° C. Solid t-butyldimethylchlorosilane (14 mg, 0.094 mmol) was added all at once and the solution was stirred at 25° C. for 15 hours. The reaction mixture was diluted with ethyl acetate and washed with 10% citric acid solution. The aqueous layer was further extracted with ethyl acetate and the combined organic extract was washed once with brine and dried over magnesium sulfate. After filtration and removal of solvent, the crude product was purified by flash chromatography (silica gel, 10% ethyl acetate in hexanes, $R_f$ 0.16) to give the 15-pivaloyl $PGF_{2\alpha}$ methyl ester 11-(t-butyldimethylsilyl) ether as a colorless oil.

$^1$H NMR(300 MHz, CDCl$_3$): δ5.25–5.5 (4H, m), 5.16 (1H, q, J=6.5 Hz), 4.05–4.1 (1H, m), 3.98 (1H, m), 3.65 (3H, s), 2.30 (2H, t, J=7.5 Hz), 1.1–2.4 (18H, m), 1.17 (9H, s, pivalate), 0.85 (12H, s+m, t-Bu+terminal CH$_3$), and 0.01 ppm (6H, s).

15-Pivaloyl $PGF_{2\alpha}$ methyl ester 11-(t-butyldimethylsilyl) ether (35.3 mg, 0.063 mmol) and 4-dimethylaminopyridine (8 mg, 0.063 mmol) were dissolved in pyridine (0.1 ml) and pivaloyl chloride (22 μl, 0.18 mmol) was added at 25° C. The solution was stirred at 25° C. for 16 hours. The volatiles were evaporated in vacuo. The residue was dissolved in ethyl acetate (20 ml) and washed with 10% citric acid and brine. The organic layer was dried over magnesium sulfate and concentrated in vacuo to leave a colorless oil. Flash chromatography (10% ethyl acetate in hexanes, $R_f$ 0.22) gave the 9,15-dipivaloyl $PGF_{2\alpha}$ methyl ester 11-(t-butyldimethylsilyl) ether.

$^1$H NMR(300 MHz, CDCl$_3$): δ5.4–5.6 (2H, m), 5.25–5.4 (2H, m), 5.11 (1H, q, J=6.5 Hz), 4.98 (1H, t, J=4 Hz), 3.85–3.95 (1H, m), 3.75 (3H, s, methyl ester), 2.2–2.4 (4H, m), 2.26 (2H, t, J=7.5 Hz), 1.9–2.1 (4H, m), 1.5–1.7 (6H, m), 1.2–1.3 (6H, m), 1.17 and 1.18 (9H each, pivalate), 0.87 (3H, distorted t, J=5 Hz), 0.82 (9H, s, t-Bu) and −0.04 ppm (6H, s).

The methyl ester obtained above (36.8 mg, 0.057 mmol) was dissolved in THF (0.28 ml) and 0.5M lithium hydroxide (0.14 ml) was added. The two-phase mixture was stirred vigorously for 14 hours at 25° C. until all the starting material was consumed. The crude reaction mixture was acidified with 10% citric acid and extracted with ethyl acetate (3×7 ml). The organic extracts were combined and dried over magnesium sulfate and concentrated to give crude 9,15-dipivaloyl $PGF_{2\alpha}$ 11-t-butyldimethylsilyl ether which was used without purification for the next step.

$^1$H NMR(300 MHz, CDCl$_3$): δ5.2–5.6 (5H, m), 5.0 (1H, t, J=5 Hz), 4.85–4.95 (1H, m), 2.25–2.4 (4H, m), 2.32 (2H, t, J=7 Hz), 1.95–2.15 (4H, m), 1.15–1.75 (11H, m), 1.19 (18H, s), 1.87 (3H, distorted t), 1.82 (9H, s) and −0.03 ppm (6H, s).

The crude product from above was dissolved in acetic acid (300 μl) and water (75 μl). The solution was heated at 50° C. with stirring under nitrogen for 18 hours. The solvent was removed in vacuo to give crude product. Flash chromatography (silica gel, 25% ethyl acetate in hexanes) gave the 9,15-dipivaloyl $PGF_{2\alpha}$.

$^1$H NMR(300 MHz, CDCl$_3$): δ5.53 (2H, ABX, $J_{AB}$=15.4, $J_{AX}$=5.9, $J_{BX}$=7.9 Hz), 5.33 (2H, ABX, $J_{AB}$=13, $J_{AX}$=5.3 and $J_{BX}$=5.8 Hz), 5.20 (1H, q, J=6 Hz), 5.10 (1H, distorted t, J=5 Hz), 3.88–3.93 (1H, m), 1.94–2.51 (6H, m), 2.31 (2H, t, J=7.3 Hz), 1.53–1.72 (6H, m), 1.23–1.37 (6H, m), 1.18, 1.20 (9H each, s, pivalate) and 0.87 ppm (3H, distorted t, J=5 Hz).

$^{13}$C NMR(75 MHz, CDCl$_3$): δ178.6, 178.5, 178.1, 133.3, 132.0, 129.9, 128.4, 76.4, 74.2, 74.0, 55.9, 47.9, 40.8, 38.8, 38.7, 34.4, 33.0, 31.3, 26.9, 26.2, 24.9, 24.6, 24.2, 22.3 and 13.7 ppm IR(CHCl$_3$, 0.1 mm): 1710, 1460, 1395, 1365, 1280, 1030, 970 and 900 cm$^{-1}$.

MS (EI on 11-trimethylsilyl ether methyl ester, m/z 608): m/z 608 (M$^+$, 0.1%), 507 (1.4), 405 (35), 315 (37), 314 (47), 264 (31), 263 (100), 216 (13), 199 (17), 159 (16) and 129 (17).

In a similar manner, the 9,15-diisobutyryl and 9,15-diisovaleryl analogs of PGF$_{2\alpha}$ were prepared.

9,15-diisobutyryl PGF$_{2\alpha}$ $^1$H NMR(300 MHz, CDCl$_3$): $\delta$5.45–5.60 (2H, m), 5.27–5.39 (2H, m), 5.21 (1H, q, J=7 Hz), 5.12 (1H, distorted t, J=5 Hz), 3.88–3.95 (1H, m), 2.27–2.60 (4H, m), 2.31 (2H, t, J=7 Hz), 1.93–2.15 (4H, m), 1.5–1.72 (6H, m), 1.22–1.38 (6H, m), 1.13–1.18 (12H) and 0.87 ppm (3H, distorted t, J=7 Hz).

$^{13}$C NMR(75 MHz, CDCl$_3$): $\delta$177.3, 176.7, 133.5, 132.0, 129.8, 128.4, 76.5, 74.2, 74.0, 55.8, 47.8, 40.8, 34.3, 34.1, 32.9, 31.3, 26.2, 24.9, 24.6, 24.2, 22.3, 18.8, 18.7 and 13.7 ppm.

MS (EI on 11-trimethylsilyl ether methyl ester, m/z 580): m/z 580 (M$^+$, 0.2%), 492 (1.5), 406 (11), 405 (35), 404 (46), 315 (39), 314 (47), 264 (31), 263 (100), 228 (11), 216 (14), 199 (16), 145 (25) and 117 (13).

9,15-Diisovaleryl PGF$_{2\alpha}$ $^1$H NMR(300 MHz, CDCl$_3$): $\delta$5.46–5.59 (2H, m), 5.29–5.39 (2H, m), 5.23 (1H, q, J=6 Hz), 5.12 (1H, distorted t, J=5 Hz), 3.88–3.95 (1H, m), 1.92–2.52 (11H, m), 2.32 (2H, t, J=7 Hz), 1.5–1.74 (6H, m), 1.23–1.33 (6H, m), 1.1–1.15 (1H, m), 0.94 (6H, d, J=6 Hz), 0.95 (6H, d, J=6 Hz) and 0.87 ppm (3H, distorted t, J=5 Hz).

$^{13}$C NMR(75 MHz, CDCl$_3$): $\delta$178.4, 173.3, 172.9, 133.7, 132.0, 129.8, 128.4, 76.4, 74.4, 74.1, 55.8, 47.4, 43.7, 43.5, 41.2, 40.9, 34.3, 33.0, 31.3, 26.6, 26.2, 25.6, 25.5, 24.9, 24.7, 24.2, 22.3, 22.2, 22.1 and 13.7 ppm.

IR(CHCl$_3$, 0.1 mm): 1720, 1466, 1373, 1296, 1261, 1242, 1192, 1169, 1123, 1096 and 972 cm$^{-1}$.

MS (EI on 11-trimethylsilyl ether methyl ester, m/z 608): m/z 608 (M$^+$, 0.1%), 507 (1.9), 406 (12), 405 (41), 404 (48), 265 (11), 315 (43), 314 (48), 264 (31), 263 (100), 228 (11), 216 (12), 199 (16), 159 (13), 145 (15), 129 (17) and 117 (13).

EXAMPLE 2

Intraocular Pressure Reducing Effect in Rabbits

Starting with PGF$_{2\alpha}$, experimental quantities of the 9,15-diisobutyryl, 9,15-diisovaleryl, and 9,15-dipivaloyl compounds were prepared in accordance with the procedure of foregoing examples. The resulting 9,15-diacyl PGF$_{2\alpha}$ compounds were added to a polysorbate carrier in amounts to produce a 0.01%, 0.1% or 1.0% solution of each ester. A group of 6–8 experimental rabbits was treated by administering approximately one drop of each solution to the surface of the eye, and intraocular pressure was measured by applanation pneumatometry (Model 30 RT manufactured by Digilab) at the time of administration and at intervals of 2, 4, 6, 8 and 10 hours thereafter. The following data were obtained:

TABLE I

INTRAOCULAR PRESSURE CHANGES AT PREDETERMINED TIMES (HR) AFTER PROSTAGLANDIN ADMINISTRATION

| Compound | PG Dose % | Time (Hours) | | | | | |
|---|---|---|---|---|---|---|---|
| | | 2 | 3 | 4 | 6 | 8 | 10 |
| Reduction in IOP (mm Hg) | | | | | | | |
| PGF$_{2\alpha}$-1-isoprop. ester | 0.01% | — | — | 1.3 | 5.8[2] | 3.5[2] | 2.9[2] |
| | 0.1% | — | — | 3.2[1] | 9.7[2] | 10.1[2] | 10.0[2] |
| 9,15-diisobutyryl PGF$_{2\alpha}$ | 0.01% | 2.2[2] | — | 0.3[2] | 0.7 | 0 | 0.8 |
| | 0.1% | 3.5[2] | — | 2.8[2] | 1.5[1] | 1.9 | 1.7 |
| | 1.0% | — | — | 3.6[1] | 7.2[2] | 7.5[2] | 7.8[2] |
| 9,15-diisovaleryl PGF$_{2\alpha}$ | 0.1% | 1.9 | — | 1.7 | 1.8 | 0.8 | 0.5 |
| | 1.0% | 0 | — | 2.0 | 1.8 | 1.7 | 1.3 |
| 9,15-dipivaloyl PGF$_{2\alpha}$ | 0.1% | 4.9[2] | — | 1.9 | 1.2 | 1.2 | 2.3 |
| | 1.0% | 2.0 | — | 3.2 | 3.5 | 1.7 | 1.7 |
| Percent Animal Exhibiting Ocular Surface Hyperemia | | | | | | | |
| PGF$_{2\alpha}$-1-isopropyl ester | 0.01% | 100 | 100 | 100 | 100 | 100 | 100 |
| | 0.1% | 100 | 100 | 100 | 100 | 100 | 87.5 |
| 9,15-diisobutyryl PGF$_{2\alpha}$ | 0.01% | 50 | — | 12.5 | 0 | 0 | 0 |
| | 0.1% | 87.5 | — | 87.5 | 87.5 | 12.5 | 0 |
| | 1.0% | 100 | — | 100 | 100 | 100 | 50 |
| 9,15-diisovaleryl PGF$_{2\alpha}$ | 0.1% | 100 | — | 50 | 50 | 33 | 0 |
| | 1.0% | 100 | — | 83 | 83 | 66 | 33 |
| 9,15-diisopivaloyl PGF$_{2\alpha}$ | 0.01% | 50 | — | 17 | 0 | 0 | 0 |
| | 0.1% | 100 | — | 100 | 83 | 67 | 17 |

1. - p < 0.05;
2. - p < 0.01

The foregoing data demonstrate that acylating both the 9 and 15 positions results in ocular anti-hypertensive activity with a reduction in ocular surface hyperemia as compared to the PGF$_{2\alpha}$-1-isopropyl ester.

What is claimed:

1. A method of treating ocular hypertension which comprises applying to the eye in an ophthalmically acceptable excipient an amount sufficient to treat ocular hypertension of the compound:

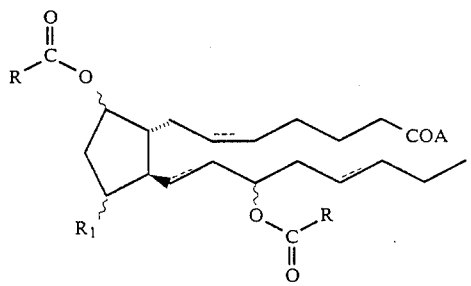

wherein the dotted lines represent a double bond in the cis or trans configuration, or a single bond; A is —OH, —O⁻X⁺ where X⁺ is a pharmaceutically acceptable cation, or —OR₂ where R₂ is lower alkyl; R₁ is —OH or =O; and the R groups are independently an acyclic hydrocarbon, saturated or unsaturated, having from 1 to 20 carbon atoms, or —(CH₂)ₙR₃ where n is 0–10 and R₃ is a hydrocarbon ring of from 3 to 7 carbon atoms or an aromatic ring.

2. The method of claim 1 where $R_1$ is —OH.

3. The method of claim 2 wherein the R groups are the same and are methyl, ethyl, propyl, butyl, pentyl or an isomeric form thereof.

4. The method of claim 3 where the C-5 and C-13 bonds are cis and trans double bonds respectively, the C-17 bond is a single bond and the C-9, C-11 and C-15 substituents are in the α configuration, the compound having the following formula:

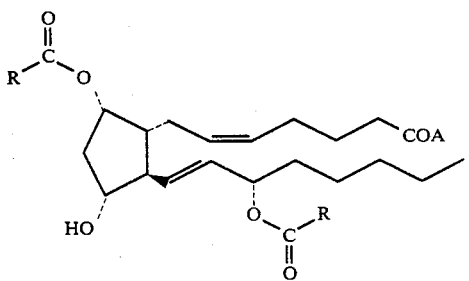

5. The method of claim 4 where the R groups are CH(CH₃)₂, the diisobutryl compound.

6. The method of claim 4 where the R groups are —CH₂CH(CH₃)₂, the diisovaleryl compound.

7. The method of claim 4 where the R groups are —C(CH₃)₃, the dipivaloyl compound.

8. The method of claim 1 where the C-5 and C-17 bonds are cis double bonds, C-13 is a trans double bond, R₁ is —OH and the C-9, C-11 and C-15 substituents are in the α configuration, the compound of the following formula:

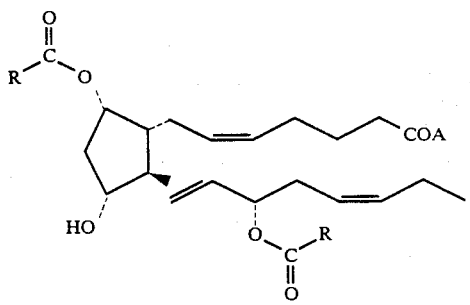

9. The method of claim 8 wherein the R groups are the same and are methyl, ethyl, propyl, butyl, pentyl or an isomeric form thereof.

10. The method of claim 1 where the C-5 and C-17 bonds are single bonds, the C-13 bond is a trans double bond, and the C-9, C-11 and C-15 substituents are in the α configuration, the compound of the following formula:

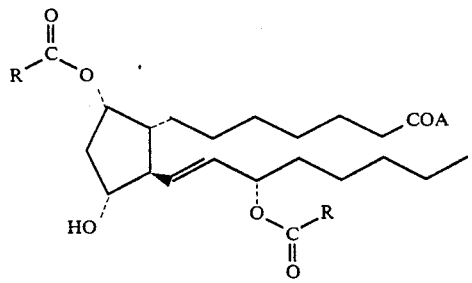

11. The method of claim 10 wherein the R groups are the same and are methyl, ethyl, propyl, butyl, pentyl or an isomeric form thereof.

12. The method of claim 1 wherein R₁ is =O and the C-5 and C-13 bonds are respectively cis and trans double bonds, C-17 is a single bond and the C-9 and C-15 substituents are in the α configuration, the compound having the following formula:

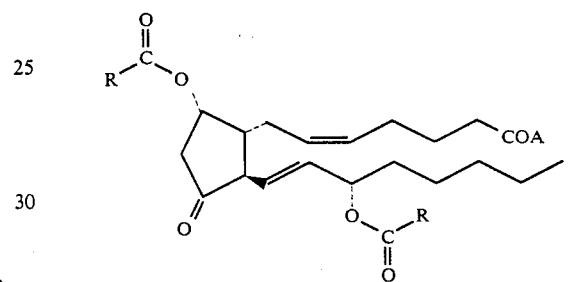

13. The method of claim 12 wherein the R groups are the same and are methyl, ethyl, propyl, butyl, pentyl or an isomeric form thereof.

14. An ophthalmically acceptable composition for reducing ocular hypertension which comprises an ophthalmically acceptable excipient and an amount sufficient to treat ocular hypertension of at least one compound of the formula:

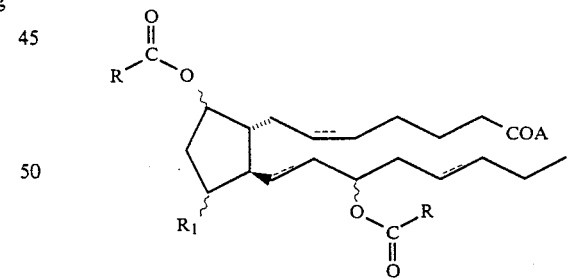

wherein the dotted lines represent a double bond in the cis or trans configuration, or a single bond; A is —OH, —O⁻X⁺ where X⁺ is a pharmaceutically acceptable cation, or —OR₂ where R₂ is lower alkyl; R₁ is —OH or =O; and the R groups are independently an acyclic hydrocarbon, saturated or unsaturated, having from 1 to 20 carbon atoms, or —(CH₂)ₙR₃ where n is 0–10 and R₃ is a hydrocarbon ring of from 3 to 7 carbon atoms or an aromatic ring.

15. The composition of claim 14 where R₁ is —OH.

16. The composition of claim 15 wherein the R groups are the same and are methyl, ethyl, propyl, butyl, pentyl or an isomeric form thereof.

17. The composition of claim 16 where the C-5 and C-13 bonds are cis and trans double bonds respectively, the C-17 bond is a single bond, and the C-9, C-11 and C-15 substituents are in the α configuration, the compound having the following formula:

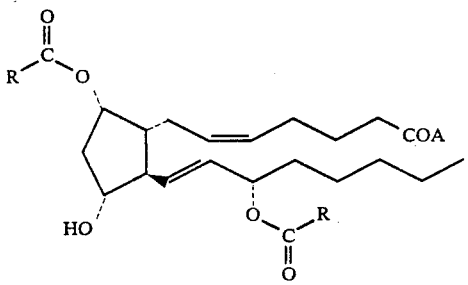

18. The composition of claim 17 where the R groups are —CH(CH$_3$)$_2$, the diisobutyryl compound.

19. The composition of claim 17 where the R groups are —CH$_2$CH(CH$_3$)$_2$, the diisovaleryl compound.

20. The composition of claim 17 where the R groups are —C(CH$_3$)$_3$, the dipivaloyl compound.

21. The composition of claim 14 where the C-5 and C-17 bonds are cis double bonds, C-13 is a trans double bond, R$_1$ is —OH, and the C-9, C-11 and C-15 substituents are in the α configuration, the compound of the following formula:

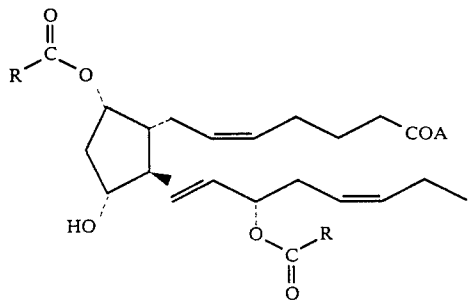

22. The composition of claim 21 wherein the R groups are the same and are methyl, ethyl, propyl, butyl, pentyl or an isomeric form thereof.

23. The composition of claim 14 where the C-5 and C-17 bonds are single bonds, the C-13 bond is a trans double bond, R$_1$ is —OH, and the C-9, C-11 and C-15 substituents are in the α configuration, the compound of the following formula:

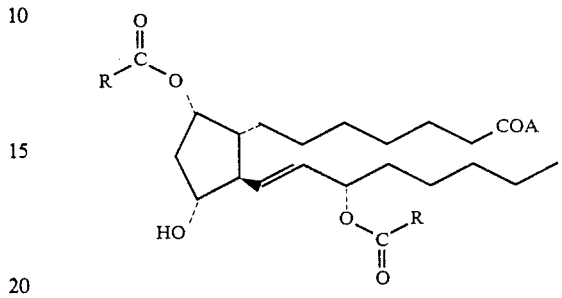

24. The composition of claim 23 wherein the R groups are the same and are methyl, ethyl, propyl, butyl, pentyl or an isomeric form thereof.

25. The composition of claim 14 wherein R$_1$ is =O and the C-5 and C-13 bonds are respectively cis and trans double bonds, the C-17 bond is a single bond and the C-9 and C-15 substituents are in the α configuration, the compound having the following formula:

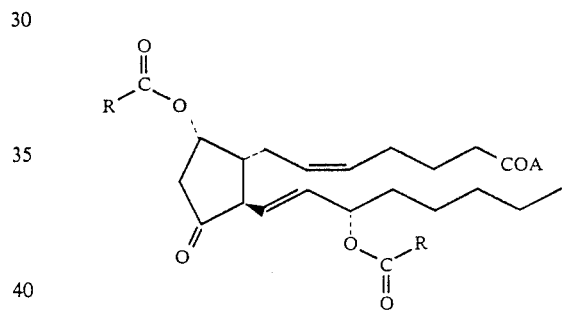

26. The composition of claim 25 where the R groups are the same and are methyl ethyl, propyl, butyl, pentyl, or an isomeric form thereof.

* * * * *